United States Patent [19]

Pedersen et al.

[11] 4,264,587
[45] Apr. 28, 1981

[54] VACCINE FOR PREVENTING PERSISTENT FELINE LEUKEMIA VIREMIA IN CATS

[76] Inventors: Niels C. Pedersen, 837 Acacia La.; Gordon H. Theilen, 882 Linden La., both of Davis, Calif. 95616

[21] Appl. No.: 62,737

[22] Filed: Aug. 1, 1979

[51] Int. Cl.³ .............................................. A61K 39/12
[52] U.S. Cl. ....................................... 424/89; 435/238
[58] Field of Search ............................ 424/89; 435/238

[56] References Cited

U.S. PATENT DOCUMENTS

| | | | |
|---|---|---|---|
| 3,966,907 | 6/1976 | Jarrett et al. | 424/89 |
| 4,034,081 | 7/1977 | Jarrett et al. | 424/89 |
| 4,086,134 | 4/1978 | Jarrett et al. | 424/89 |
| 4,117,112 | 9/1978 | Jarrett et al. | 424/89 |

OTHER PUBLICATIONS

Pedersen et al., Am. J. Vet. Res. 40 (8): 1120–1126, Aug. 1979 (copyright 1978), citing.
Jarrett et al., Int. J. Cancer 16: 134–141 (1975).
Jarrett et al., Nature 248: 230–232, (1976).
Yohn et al., Cancer Res. 36: 646–651 (1976).
Schaller et al., J. Natl. Cancer Inst. 59: 1441–1450 (1970).
Olsen et al., Cancer Res. 35: 3642–3646 (1976).
Olsen et al., Cancer Res. 37: 2082–2085 (1977).
Hoover et al., Infection and Immunity 16 (1): 54–59 Apr. 1977.
Salerno et al., P.S.E.B.M., 160: 18–23 (1979).

*Primary Examiner*—Shep K. Rose

[57] ABSTRACT

A vaccine in parenteral dose form for preventing persistent feline leukemia viremia in cats is characterized by containing as the immunizing agent inactivated feline leukemia virus (FeLV) derived from the FL74 feline lymphoblastoid cell line.

17 Claims, No Drawings

VACCINE FOR PREVENTING PERSISTENT FELINE LEUKEMIA VIREMIA IN CATS

BACKGROUND AND PRIOR ART

Feline leukemia virus (FeLV) was first isolated in 1964 from cats with lymphoid malignancies. It was subsequently shown that a proportion of cats inoculated with FeLV would develop lymphoid neoplasms after a latent period of many weeks or months. In 1970, a simple blood test was developed to detect cats that were infected with FeLV. After screening many cats, it became apparent that lymphoid tumors represented only a fraction of the disease caused by FeLV. Conditions related to FeLV infection included anemia, myeloproliferative disorders, and reproductive problems in queens. In addition, a marked proportion of cats suffering from a wide range of infective diseases were found to be concurrently infected with FeLV. The pathogenesis of FeLV infection in nature has been the topic of many reports. In the cat population, FeLV appears to be widespread, and horizontal transmission from cat to cat is apparently the major mode of infection. After exposure, cats develop immunity to the virus or become chronically infected. Many of the chronically infected cats eventually succumb from various disorders, but others remain asymptomatic for extended periods. Pedersen et al, Am. J. Vet. Research, 38, 1523-1531 (1977).

The morbidity and mortality from FeLV infection is related to the density of the cat population study. The virus is prevalent in urban areas, and in multiple cat households and catteries. In these environments almost all exposed cats will become infected, and 30% or more of them will become persisently viremic. Hardy et al, Nature, 244, 266-267 (1973). Therefore, a vaccine which was capable of preventing persistent feline leukemia viremia would be of great value.

Previous attempts to prepare vaccines for feline leukemia have been directed to preventing the FeLV infection, and/or the tumors which may develop if a persistent infection develops. The effectiveness of vaccines for feline leukemia have been evaluated in terms of the serum antibody titer to feline oncorna virus-associated cell membrane antigen (FOCMA), and virus neutralizing antibody titer (VN), or by challenge of inoculated cats with injections of virulent feline sarcoma virus (FeSV) or virulent FeLV. No study has been reported in which the effectiveness of feline leukemia vaccines for preventing persistent infection has been specifically evaluated, and there is no report of a challenge test by natural infection.

It has been reported that an effective vaccine against feline leukemia virus can use a cell membrane antigen system. Jarrett et al, Int. J. Cancer, 16, 134-141 (1975). The cell-type vaccines of Jarrett et al were prepared from a feline lymphoblastoid cell line permanently infected with FeLV (the FL74 cell line). FOCMA antibody titers were determined after administration of the FL74 cell vaccines for both live cells and cells treated with formaldehyde. Tests were also made with FeLV produced by the FL74 cells and separated from the cells for vaccine preparation. However, Jarrett et all concluded: "The high antigenicity of intact FL74 cells and, in contrast, the very low antigenicity of the virus purified from those cells, were shown in the present experiments. The purified virus failed to induce any demonstrable antibody in cats which had not been previously exposed."

U.S. Pat. No. 3,966,907 of Jarrett et al appears to be based on the research reported in the above-cited publication of Jarrett et al. It primarily discloses vaccines against feline leukemia which comprise cells infected with FeLV which have virus-associated antigen on their surfaces. However, in Example 7, a vaccine prepared from FeLV particles separated from cells is described. The viruses are treated for inactivation with 0.05% formalin, and are combined with Freund's incomplete adjuvant to prepare the vaccine dose, which contained approximately $10^7$ virus particles. On a protein weight basis, this is equivalent to about 0.001 to 0.002 milligrams of protein. There are also other reports in the literature of feline leukemia vaccines prepared from inactivated FeLV. See Yohn et al, Cancer Res., 36, 646-651 (1976); and Schaller et al, J. Natl. Cancer Inst., 59, 1441-1450 (1970). Yohn et al reported that no protection was provided by the vaccine, while Schaller et al found that the cats became more susceptible to tumor induction. With virus infected cell vaccines, Olsen et al reported that vaccinated cats are resistent to FeSV tumor induction but not to feline leukemia virus infection. Cancer Res., 35, 3642-3646 (1976).

SUMMARY OF INVENTION

The present invention is based in part on the discovery that inactivated feline leukemia virus (FeLV) can be used to prepare a vaccine which has a high level of effectiveness in preventing persistent feline leukemia viremia. During the experimental work leading to the present invention, it was found that when a sufficient concentration of formaldehyde was used to completely inactivate FeLV or FL74 cells that neither produced a vaccine which gave significant FOCMA or virus neutralizing antibody responses. Further, neither type of vaccine prevented kittens from being naturally infected with virulent FeLV. However, the inactivated FeLV vaccine was much more effective than the cell vaccine in preventing persistent viremia. Therefore, vaccines prepared in accordance with the present invention can be used to control and reduce persistent feline leukemia viremia, which is the major problem associated with FeLV infection. The details for preparing vaccines in accordance with the present invention will now be described.

DETAILED DESCRIPTION

The vaccines of the present invention are prepared by culturing cells infected with feline leukemia virus (FeLV), such as feline lymphoblastoid cells replicating FeLV. The virus produced by the cells should provide antigens of Types A, B, and C, as described by Sarma et al, Virology, 54, 160-169 (1973). The FL74 feline lymphoblastoid cell line, and cell lines produced therefrom meet this criteria. The FL74 cell line and related cell lines are available in many university laboratories in the United States and other countries. See Theilen et al, Nature, 222, 589-590 (1969); Essex et al, J. Nat. Cancer Inst. 54, 631-635 (1975); and Jarrett et al, Int. J. Cancer, 16, 134-141 (1975). As originally described in the cited publication of Theilen et al, the infected lymphoblastoid cells elaborate FeLV particles into the culture medium in which they are grown, as well as producing pre-viral antigens associated with the cell membranes. Immature virus particles grow as buds on the cell membranes, and are released into the media as mature viral particles.

The FL74-derived cell line which is preferred for practicing the present invention was developed by four years of continuous laboratory culture passage. It is identified by the code designation FL74-UCD-1, and is now further identified by deposit with the American Type Culture Collection, Rockville, Maryland, under ATCC No. CrL-8012). The virus produced by the original FL74 cell line has been referred to as KT-FeLV, and correspondingly the virus produced by FL74-UCD-1 is identified as KT-FeLV-UCD-1. The KT-FeLV-UCD-1 virus has attenuated virulence for cats. However, when inactivated in accordance with the present invention and prepared in vaccine form, the viral particles (separate from the cells from which they are produced) are capable of preventing persistent feline leukemia viral infection.

The FL74 cells or cell lines derived therefrom may be grown in a suitable aqueous nutrient medium, such as the Leibovitz L-15 medium. See Leibovitz, Amer. J. Hyg. 78, 173 (1963). For maximizing the viral yield, the medium preferably contains fetal calf serum. For example, the Leibovitz medium may contain from 15 to 30% (by volume) of the fetal calf serum. The culturing can be carried out by standard cell culture techniques, such as a suspension culture in roller bottles. The first phase of the culturing can be carried out over a period of several days, such as three to four days. Following the initial phase, the culture medium and cells can be subjected to centrifugation to separate the cells. The pelleted cells are separated from the supernatant culture fluid containing the FeLV formed in the first phase. However, during the first culturing period, the elaboration of viral particles into the media is at a relatively low level. Much greater virus production is obtained by resuspending the pelleted cells in fresh media, and continuing to culture the cells for a second period, such as for a period of three or more days. During the second culture period, very little additional cell growth takes place, but virus production occurs at a high level. The cells and cell debris are pelleted out of the second culture medium by centrifugation, and separated therefrom. The tissue culture fluid from both culturings can then be combined to provide the stock of FeLV to be used for preparing vaccine.

After removal of the cells and large particulate debris, the supernatant fluid can be further purified by centrifugation at higher gravity, such as $6,000 \times g$, thereby pelleting and removing most of the subcellular debris. The FeLV can then be recovered from the supernatant fluid by centrifugation at a very high gravity force, for example, centrifuging at 20,000 rpm in a Beckman Type 21 batch type rotor for 90 minutes. The resultant pellet will contain all of the virus particles plus a small amount of subcellular debris. The intact viral particles have a buoyant density of 1.016 grams per milliliter (gm/ml) determined by density gradient separation against sucrose.

In preparing the vaccine, the separated viral particles are inactivated. While other known inactivation procedures can be used, formaldehyde inactivation is preferred. When the FeLV is inactivated in the presence of a sufficient concentration of formaldehyde, the antigenic potency of the vaccine is improved. Treatment with aqueous formaldehyde at a concentration of from 0.3 to 1.8% is preferred, and optimum results appear to be obtained within the range from about 0.5 to 1.5% formaldehyde. In carrying out the inactivation treatment, the separated FeLV can be resuspended in aqueous formaldehyde at the selected concentration, the volume of the formaldehyde solution being determined so as to correspond with the desired administration concentration of the FeLV after the formaldehyde solution is combined with a suitable adjuvant. For example, each milliliter (ml) of the solution may contain from 0.04 to 3.2 milligrams (mg) of virus on a protein basis. Then when 0.25 ml of the solution containing the inactivated virus is combined with 0.25 ml of an adjuvant, the resulting 0.5 ml dose will contain from 0.01 to 0.8 mg of the inactivated virus. The preferred dose level appears to be about 0.02 to 0.4 mg of inactivated FeLV (protein basis) per dose. This amount is particularly effective when potentiated by the formaldehyde treatment, and when combined with a suitable adjuvant. Preferably, therefore, each vaccine dose should contain at least 0.02 mg of the inactivated virus.

Various standard adjuvants can be used, such as Freund's incomplete adjuvant, or an aluminum hydroxide adjuvant. Freund's incomplete adjuvant can be obtained from Difco Laboratories, Detroit, Michigan, or it may be prepared by combining mannide monooleate with pariffin oil in the proportions by volume of 1.5:8.5. Aluminum hydroxide adjuvants can be prepared as described in U.S. Pat. No. 3,149,036. A commercial form of this adjuvant is sold by Merck & Co., Inc., Rahway, N. J., as Merck Adjuvant 65. While the proportions of adjuvant to the virus-containing formaldehyde solution can vary considerably, approximately equal proportions are convenient and desirable.

The preparation and use of vaccines prepared in accordance with the present invention are further illustrated by the following examples.

EXAMPLE I

Culture Procedure

The FL74-UCD-1 cell line (ATCC No. CrL-8012), is cultured for production of the associated KT-FeLV-UCD-1 strain of feline leukemia virus. This line was obtained by four years of continuous laboratory culture passage from the original KT-FeLV replicating lymphoblastoid cells, later referred to as the F74 cell line. See Theilen et al, Nature, 222, 589–590 (1969); and Jarrett et al, J. Nat. Cancer Inst. 51, 261–263 (1973). The FL74-UCD-1 cell line produces large amounts of feline leukemia virus (FeLV), which it elaborates continuously into the tissue culture media. This elaborated virus is of attenuated virulence for cats. The cells can be grown in Leibovitz's 15 (L15) media with 15% (by volume) fetal calf serum, in roller bottles as a suspension culture. Cell numbers are reduced by one-fourth when the cell concentration reaches $5 \times 10^6$ to $1 \times 10^7$ cells per ml. Maximum virus production is achieved by the following passage schedule: Following the initial culture split, cell numbers are allowed to return to around $5 \times 10^6$ to $1 \times 10^7$ cells/ml, which is usually after 3-4 days in culture. At this time the culture fluid is centrifuged to pellet all of the cells, and the supernatant culture fluid removed. The old culture fluid is replaced with an equal volume of fresh media, and the cells are allowed to grow in the media for three more days. Very little additional cell growth takes place during this period, but virus production occurs at a high level. Tissue culture fluid harvested from both the split and feeding passages is utilized for virus collection.

Virus Collection

The KT-FeLV-UCD-1 virus can be purified from tissue culture fluid as follows:

1. Cells and large particulate debris are removed by centrifugation at 1,200×g for 10 minutes.
2. Supernatant fluid is then centrifuged at 6,000×g for 45 minutes to remove most of the subcellular debris.
3. Supernatant fluid from Step 2 is then centrifuged at 20,000 rpm in a Beckman Type 21 batch type rotor for 90 minutes. This can also be done with oher high speed centrifuge rotors exerting a high g force. The resultant pellet contains all of the virus particles plus a small amount of subcellular debris. One liter of the original tissue culture fluid will yield 1 to 2 mg of purified virus.

Preparation of FeLV Vaccine

The KT-FeLV-UCD-1 vaccine can be produced as follows:

1. The pelleted virus from Step 3 of the virus collection procedure, as described above, is resuspended in an isotonic buffered salt solution such as phosphate buffered saline, Puck's saline, Tris-saline, or similar solutions (pH=7.4), so that 0.1 to 0.2 mg of virus (protein basis) is present in 1 ml of the buffered salt solution. This concentration is designated 100 ml equivalents (ml eq)/ml, indicating that the virus originally present in 100 ml of tissue culture fluid is now present in 1 ml. The amount of virus can be varied from 50 to 800 ml eq/ml, depending on the strength of the vaccine that is desired.
2. Thirty lambda ($\mu l$) of formalin solution (33% formaldehyde) is added to each 1 ml of the virus suspension, and the mixture allowed to stand for 12-24 hours at 4° C. The effective formaldehyde concentration of the mixture is approximately 1%. After the formaldehyde has reacted with the virus, the mixture is either lyophilized in 0.25 ml aliquots or used immediately.

The vaccine as prepared for administration can be comprised of 0.25 ml of the 1% formaldehyde inactivated virus suspension, plus 0.25 ml of Freund's incomplete adjuvent to give a 0.5 ml injection dose. Alternatively, 0.25 ml of AlOH gel can be used as an adjuvant. The amount of actual virus protein in each 0.25 ml dose of virus suspension varies depending on the concentration factor. As an example, if the virus suspension was 100 ml eq (0.1 to 0.2 mg virus) per ml, then 0.25 ml would provide 25 ml eq or 0.25 to 0.050 mg virus protein in each 0.5 ml vaccine dose after adjuvant addition.

Administration Procedure

One 0.5 ml dose of vaccine in adjuvant, prepared as described above, can be given intramuscularly to kittens at 10-16 weeks of age. One dose of vaccine contains 0.25 ml of the inactivated virus suspension and 0.25 ml of the adjuvant. A second dose of the same vaccine is similarly given 3-4 weeks later. A booster injection given at one-year intervals also may be advantageous.

EXAMPLE II

In a pilot experiment to determine the effect of using different concentrations of formaldehyde for the FeLV inactivation, equal amounts of FeLV, prepared as described in Example I, were treated with different formaldehyde solutions. The dose level amounts of the virus thus treated were not precisely deterimined, but were estimated to contain from 0.2 to 0.4 mg of virus on a protein basis. The equal dose level amounts of FeLV were suspended in 0.5 ml of aqueous formaldehyde at respective concentrations of 0.1, 0.5, 1.0, and 2.0% formaldehyde. After holding in the formaldehyde solutions for 24 hours at 4° C., the 0.5 ml dose quantities were mixed with 0.5 ml of Freund's incomplete adjuvant, thereby providing injection doses of approximately 1.0 ml. Individual kittens were then given three successive doses of vaccine at the same formaldehyde treatment level with three week intervals between doses. Two kittens were used for the 1.0 and 2.0% formaldehyde levels, and one kitten for the 0.1 and 0.5% levels. Antibody titers were measured 2 weeks after the third dose of vaccine. The FOCMA titer was determined by the method of Essex et al, Nature, 233, 195-196 (1971), and the virus neutralizing antibody titer (VN) was determined by the modified method described in Pedersen et al, Am. J. Vet. Res., 38, 1523-1531 (1977). The results are summarized below in Table A.

TABLE A

| Concentration of Formaldehyde in Vaccine | FOCMA Antibody Titer | VN Antibody Titer |
|---|---|---|
| 0.1% | negative | negative |
| 0.5% | + > 1:5 | + 1:40 |
| 1.0% | + > 1:5 | + 1:160 |
| 1.0% | + > 1:5 | + 1:160 |
| 2.0% | + > 1:5 | + 1:160 |
| 2.0% | + > 1:5 | ± 1:10 |

We claim:

1. The method of protecting cats and kittens against diseases resulting from infection with feline leukemia virus (FeLV) in which FeLV is obtained by culturing FL74 feline lymphoblastoid cells, separating the FeLV from the cells, inactivating the FeLV, and vaccinating the cat or kitten with inactivated FeLV, wherein the improvement comprises inactivating the FeLV by contact with an aqueous solution of formaldehyde having a concentration of from 0.3 to 1.8% formaldehyde, and protecting the cat or kitten against persistent leukemia viremia by vaccinating the cat or kitten with a plurality of successive doses of from 0.01 to 0.8 milligrams (mg) per dose of said inactivated FeLV (protein basis).

2. The improved method of claim 1 in which each vaccine dose contains from 0.02 to 0.4 mg of said FeLV (protein basis) and said doses are administered to kittens.

3. The improved method of claim 1 or claim 2 in which said FeLV is obtained by culturing the FL74-UCD-1 cell line (ATCC No. CRL-8012).

4. The method of protecting kittens against diseases resulting from infection with feline leukemia virus (FeLV) in which FeLV is obtained by culturing FL74 feline lymphoblastoid cells, separating the FeLV from the cells, inactivating the FeLV, and vaccinating the cat or kitten with the inactivated FeLV in admixture with an adjuvant, wherein the improvement comprises protecting the cat or kitten against persistent leukemia viruemia by the steps of inactivating the FeLV obtained from said culturing by introducing the FeLV into an aqueous solution of formaldehyde having a concentration of from 0.3 to 1.8% formaldehyde, and vaccinating the cat or kitten with a plurality of successive doses of from 0.02 to 0.4 milligrams (mg) of said inactivated FeLV (protein basis).

5. The improved method of claim 4 in which the formaldehyde concentration of said aqueous solution used from said FeLV inactivation is from 0.5 to 1.5% formaldehyde.

6. The improved method of claim 4 or claim 5 in which said FeLV is obtained by culturing the FL74-UCD-1 cell line (ATCC No. CRL-8012).

7. The improved method of claim 4, claim 5, or claim 6 in which said adjuvant is Freund's incomplete adjuvant.

8. The improved method of claim 4 or claim 5 in which said FeLV is obtained by culturing the FL74-UCD-1 cell line (ATCC No. CRL-8012), and in which said adjuvant is Freund's incomplete adjuvant.

9. The process of preparing a vaccine for prevention of persistent feline leukemia viremia, in which FL74 feline lymphoblastoid cells are cultured in a medium with elaboration of feline leukemia virus (FeLV) into the medium, separating the cells from the medium, and recovering the active FeLV, wherein the improvement comprises enhancing the antigenic response to said vaccine by inactivating the recovered FeLV in an aqueous solution of formaldehyde having a concentration of from 0.3 to 1.8% formaldehyde.

10. The process improvement of claim 9 in which said aqueous solution has a formaldehyde concentration of from 0.5 to 1.5%.

11. The process improvement of claim 9 or claim 10 in which said FL74 cells are provided by the FL74-UCD-1 cell line (ATCC No. CRL-8012).

12. The process of preparing a vaccine for prevention of persistent feline leukemia viremia, in which FL74 feline lymphoblastoid cells are cultured in a medium with elaboration of feline leukemia virus (FeLV) into the medium, separating the cells from the medium, and recovering the active FeLV, wherein the improvement comprises enhancing the antigenic potency of said vaccine by the steps of inactivating the recovered FeLV in an aqueous solution of formaldehyde having a concentration of from 0.3 to 1.8% formaldehyde, and preparing the inactivated FeLV in injectable dose form by combining the FeLV with an adjuvant therefor, said injectable dose form containing from 0.1 to 0.8 milligrams (mg) of FeLV (protein basis) per 0.5 milliliter (ml) of dose.

13. The vaccine dose form prepared by the process of claim 12.

14. The improved process of claim 24 or the vaccine dose of claim 13 in which said dose form is prepared by combining said adjuvant with said FeLV-containing formaldehyde solution.

15. The process of preparing a vaccine for preparation of persistent feline leukemia viremia, in which FL74 feline lymphoblastoid cells are cultured in a medium with elaboration of feline leukemia virus (FeLV) into the medium separating the cells from the medium, and recovering the active FeLV, wherein the improvement comprises enhancing the antigenic potency of said vaccine by the steps of using the FL74-UCD-1 cell line (ATCC No. CRL-8012) to prepare said active FeLV, inactivating the recovered FeLV in an aqueous solution of formaldehyde having a concentration of from 0.5 to 1.5% formaldehyde, and preparing the inactivated FeLV in injectable dose form by combining the FeLV with Freund's incomplete adjuvant, said injectable dose form containing from 0.2 to 0.4 milligrams (mg) of FeLV (protein basis) per 0.5 milliliter (ml) of dose.

16. The improved process of claim 15 in which said dose form is prepared by combining said Freund's incomplete adjuvant with said FeLV-containing formaldehyde solution.

17. The vaccine dose form prepared by the process of claim 15 or claim 16.

* * * * *